US008877139B2

(12) United States Patent
Diersing et al.

(10) Patent No.: US 8,877,139 B2
(45) Date of Patent: Nov. 4, 2014

(54) COMPOSITIONS COMPRISING A FUNCTIONAL PERFUME COMPONENT MIXTURE

(75) Inventors: Steven Louis Diersing, Cincinnati, OH (US); Rhonda Jean Jackson, Cincinnati, OH (US); George Kavin Morgan, III, Hamilton, OH (US); Jason John Olchovy, West Chester, OH (US)

(73) Assignee: The Procter & Gamble Company, Cincinnati, OH (US)

(*) Notice: Subject to any disclaimer, the term of this patent is extended or adjusted under 35 U.S.C. 154(b) by 380 days.

(21) Appl. No.: 12/855,804

(22) Filed: Aug. 13, 2010

(65) Prior Publication Data

US 2012/0039753 A1  Feb. 16, 2012

(51) Int. Cl.

| A61L 9/00 | (2006.01) |
|---|---|
| A24F 25/00 | (2006.01) |
| C09K 5/00 | (2006.01) |
| A61L 9/015 | (2006.01) |
| A61L 9/04 | (2006.01) |
| A61L 9/01 | (2006.01) |
| A61L 9/12 | (2006.01) |

(52) U.S. Cl.
CPC .. *A61L 9/01* (2013.01); *A61L 9/127* (2013.01)
USPC .............. 422/306; 239/34; 239/44; 424/76.2; 424/76.4; 96/222

(58) Field of Classification Search
CPC ............. A61L 2/22; A61L 9/00; A61L 9/014; A61L 9/037; A61L 9/04; A61L 9/127; C09F 7/00; B01B 1/005
USPC .................. 422/123, 5, 120, 306; 239/34, 44; 252/67; 424/76.2, 76.4; 96/222
See application file for complete search history.

(56) References Cited

U.S. PATENT DOCUMENTS

| 4,561,997 A | 12/1985 | Roehl |
|---|---|---|
| 4,649,046 A | 3/1987 | Kross |
| 4,663,081 A * | 5/1987 | Grimshaw et al. ................ 512/3 |
| 4,671,959 A | 6/1987 | Warren et al. |
| 4,956,342 A | 9/1990 | Christenson et al. |
| 7,014,127 B2 | 3/2006 | Valpey, III et al. |
| 8,338,346 B2 | 12/2012 | Diersing et al. |

FOREIGN PATENT DOCUMENTS

| EP | 0 177 255 A2 | 4/1986 |
|---|---|---|
| EP | 0 695 552 A1 | 2/1996 |
| GB | 2 260 494 A | 4/1993 |
| JP | 10137140 | 5/1980 |
| WO | WO 89/08462 A1 | 9/1989 |
| WO | WO 00/05948 A1 | 2/2000 |
| WO | WO 03/033038 A1 | 4/2003 |

* cited by examiner

*Primary Examiner* — Monzer R Chorbaji
(74) *Attorney, Agent, or Firm* — Amy I Ahn-Roll

(57) ABSTRACT

Compositions having a mixture of functional perfume components are provided. In one embodiment, the functional perfume components comprise iso-nonyl acetate, dihydro myrcenol, linalool, and benzyl acetate. In one embodiment, the functional perfume component may be present in an amount from about 75% to about 100%, by weight of said mixture, wherein said composition is substantially free of a VOC.

3 Claims, 1 Drawing Sheet

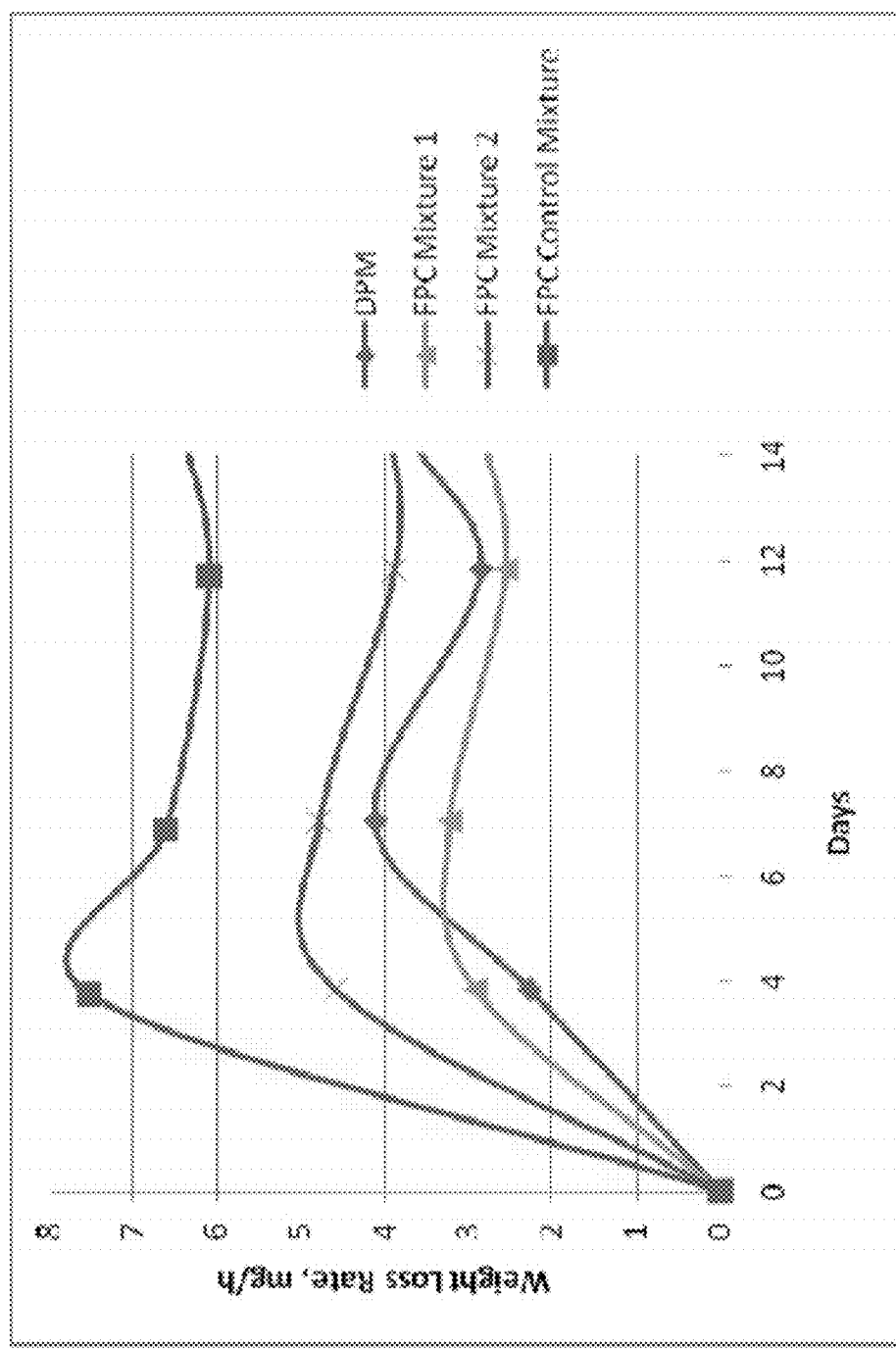

COMPOSITIONS COMPRISING A FUNCTIONAL PERFUME COMPONENT MIXTURE

FIELD OF THE INVENTION

The present invention relates to compositions comprising a mixture of functional perfume components.

BACKGROUND OF THE INVENTION

Various perfume compositions are available to mask, deodorize, and/or remove malodors in the air. These compositions may be dispensed by air freshening systems, including electrical (i.e. energized) plug-in diffusers, passive (i.e. non-energized) diffusers, trigger spray dispensers, and aerosol spray dispensers. In many instances, adequate delivery of perfume compositions into the air requires the use of evaporation or dispensing aids.

Passive or diffusive air fresheners, for example, may utilize liquid compositions containing 20% or more volatile organic compounds ("VOCs") as a perfume evaporation aid. "VOCs" as used herein means volatile organic compounds that have a vapor pressure of greater than 0.2 mm Hg measured at 20° C. and aid in perfume evaporation. Exemplary VOCs include the following organic solvents: dipropylene glycol methyl ether ("DPM"), 3-methoxy-3-methyl-1-butanol ("MMB"), volatile silicone oil, and dipropylene glycol esters of methyl, ethyl, propyl, butyl, ethylene glycol methyl ether, ethylene glycol ethyl ether, diethylene glycol methyl ether, diethylene glycol ethyl ether, or any VOC under the tradename of Dowanol™ glycol ether.

In passive and energized air diffusers, DPM and MMB are commonly used. In aerosol dispensers, a commonly used dispensing aid or propellant is hydrocarbon, which is a VOC. VOCs may be undesirably in some product applications given its solventy smell. Additionally, some VOCs are currently regulated by the Environmental Protection Agency and California Air Resource Board ("CARB"). VOCs, classified by CARB regulations, can be found in Article 2, §94508(a)(144) of the California Consumer Products Regulation. In view of the aforementioned concerns and the desire to protect the environment, approaches for reducing VOC content are desirable.

One approach for reducing the VOC content is to simply lower the amount of VOCs in the formulation. However, lowering the VOC content can adversely affect performance. For example, in passive and energized air diffusers, VOCs may aid in keeping perfume components in solution which aids in evaporation profiles of the solution as it diffuses from the diffuser. As such, reducing the VOC level may compromise the delivery of an intended perfume character. In the case of aerosol spray dispensers, reducing the propellant content may leave product in the dispenser even after the propellant has been depleted. It may also increase the particle size of the dispensed product, which can lead to excessive surface deposition. Another approach for reducing VOC content in aerosol spray dispensers is outlined in U.S. Pat. No. 7,014,127. This approach utilizes at most 25% of a liquefied gas propellant, free of butane, in combination with a specific range of can pressures and valve orifice dimensions.

As such, there continues to be a need for improved compositions, including air freshening compositions, having components that provide continuous fragrance yet are substantially free of VOCs.

SUMMARY OF THE INVENTION

In one embodiment of the present invention, there is provided a composition having a perfume mixture that includes a mixture of functional perfume components ("FPCs" or singularly, "FPC"). The FPCs comprise iso-nonyl acetate, dihydromyrcenol, linalool, and benzyl acetate. The composition is substantially free of a VOC.

In another embodiment of the present invention, there is provided a composition comprising a perfume mixture that includes a FPC mixture. The FPC mixture includes, by weight of the perfume mixture, about 5% to about 10% of benzyl acetate; about 5% to about 35% of iso-nonyl acetate; about 20% to about 45% dihydro myrcenol; and about 35% to about 45% linalool. The composition is free of a VOC.

In yet another embodiment of the present invention, there is provided an air freshening apparatus comprising an evaporative substrate consisting of wicks, membranes, or combinations thereof; and a reservoir for containing a composition that includes a perfume mixture. The perfume mixture includes a FPC mixture that includes iso-nonyl acetate, dihydro myrcenol, linalool, and benzyl acetate.

BRIEF DESCRIPTION OF THE DRAWINGS

FIG. 1 is a line graph illustrating the evaporation profile of a mixture of FPCs, according to one embodiment of the present invention, compared to a composition having a mixture of perfume materials and compared to a traditional organic solvent.

DETAILED DESCRIPTION OF THE INVENTION

The terms "air freshening composition" or "air freshener", as used herein, refer to any suitable composition that reduces odors in air, and/or reduces the impression of odors in the air by masking, layering or including malodor counteractant perfume raw materials into the composition.

"VOCs" as used herein means volatile organic compounds that have a vapor pressure of greater than 0.2 mm Hg measured at 20° C. and aid in perfume evaporation.

The present invention relates to a composition comprising a mixture of FPCs. The present invention eliminates or reduces the need for ingredients or materials that have VOCs that are able to aid in perfume evaporation.

The composition may be substantially free of VOCs, meaning it has no more than about 18%, alternatively no more than about 6%, alternatively no more than about 5%, alternatively no more than about 1%, alternatively no more than about 0.5%, by weight of the composition, of VOCs. The composition, in some embodiments, may be free of VOCs.

FPCs

FPCs of the present invention are a class of perfume raw materials with evaporation properties that are similar to traditional organic solvents or VOCs commonly used in air freshening compositions. The FPCs of the present invention aid in the evaporation of perfume raw materials and, in a mixture, provide a hedonic, fragrance benefit. FPCs may be used in relatively large concentrations without negatively impacting perfume character of the overall composition.

It has been understood that perfume raw material generates an olfactory response in the individual smelling the perfume. The minimum concentration of perfume ingredient which is consistently perceived to generate an olfactory response in an individual is known as the odor detection threshold ("ODT"). As the concentration of perfume is increased, so are the odor intensity of the perfume and the olfactory response of the individual. This continues until the concentration of the perfume reaches a maximum, at which point the odor intensity reaches a plateau beyond which there is no additional olfactory response by the individual. This range of perfume concentration through which the individual consistently perceives an odor is known as the Odor Detection Range ("ODR"). The concentration of perfume raw materials in a composition should be formulated less than or equal to the ODT or within the ODR of the perfume raw materials, since compositions comprising higher levels are costly and inefficient.

The Applicants have, however, found that in some circumstances it may be desirable to utilize FPCs that exceed the ODT, alternatively that exceed the ODR. Specifically, the use of these FPCs at higher levels than traditionally used in air freshening compositions and without the presence of a traditional organic solvent, surprisingly, provides continuous fragrance to the atmosphere.

Perfume raw materials that are suitable as a FPC can be defined using Kovat's Index ("KI"). The KI places the volatility attributes of an analyte (e.g. component of a volatile composition) on a gas chromatography column in relation to the volatility characteristics of an n-alkane (normal alkane) series on that column. A typical gas chromatograph ("GC") column is a DB-5 column available from Agilent Technologies of Palo Alto, Calif. By this definition, the KI of a normal alkane is set to 100n, where n is the number of carbon atoms in the n-alkane. The KI of an analyte, x, eluting at time t', between two n-alkanes with number of carbon atoms "n" and "N" having corrected retention times $t'_n$ and $t'_N$ respectively, will then be calculated as:

$$KI = 100\left(n + \frac{\log t'_x - \log t'_n}{\log t'_N - \log t'_n}\right)$$

On a non-polar to slightly polar GC stationary phase, KI of analytes are correlated with their relative volatility. For example, analytes with smaller KIs tend to be more volatile than those with larger KIs. Ranking analytes with their corresponding KI values gives a good comparison of analyte evaporation rates in liquid-gas partitioning systems.

A suitable FPC may have a Kovat's index from about 900 to about 1400, alternatively about 900 to about 1200, alternatively about 1000 to about 1100, alternatively about 1000.

Perfume raw materials that are suitable for use as a FPC can also be defined using ODT and non-polarizing scent character for a given perfume character scent camp. ODTs may be determined using a commercial gas chromatograph ("GC") equipped with flame ionization and a sniff-port. The GC is calibrated to determine the exact volume of material injected by the syringe, the precise split ratio, and the hydrocarbon response using a hydrocarbon standard of known concentration and chain-length distribution. The air flow rate is accurately measured and, assuming the duration of a human inhalation to last 12 seconds, the sampled volume is calculated. Since the precise concentration at the detector at any point in time is known, the mass per volume inhaled is known and concentration of the material can be calculated. To determine whether a material has a threshold below 50 ppb, solutions are delivered to the sniff port at the back-calculated concentration. A panelist sniffs the GC effluent and identifies the retention time when odor is noticed. The average across all panelists determines the threshold of noticeability. The necessary amount of analyte is injected onto the column to achieve a 50 ppb concentration at the detector. Typical gas chromatograph parameters for determining odor detection thresholds are listed below. The test is conducted according to the guidelines associated with the equipment.

Equipment:
  GC: 5890 Series with FID detector (Agilent Technologies, Ind., Palo Alto, Calif., USA)
  7673 Autosampler (Agilent Technologies, Ind., Palo Alto, Calif., USA)
  Column: DB-1 (Agilent Technologies, Ind., Palo Alto, Calif., USA)
  Length 30 meters ID 0.25 mm film thickness 1 micron (a polymer layer on the inner wall of the capillary tubing, which provide selective partitioning for separations to occur)

Method Parameters:
  Split Injection: 17/1 split ratio
  Autosampler: 1.13 microliters per injection
  Column Flow: 1.10 mL/minute
  Air Flow: 345 mL/minute
  Inlet Temp. 245° C.
  Detector Temp. 285° C.
  Temperature Information
  Initial Temperature: 50° C.
  Rate: 5 C/minute
  Final Temperature: 280° C.
  Final Time: 6 minutes
  Leading assumptions: (i) 12 seconds per sniff
    (ii) GC air adds to sample dilution Suitable FPCs may have an ODT from greater than about 1.0 ppb, alternatively greater than about 5.0 ppb, alternatively greater than about 10.0 ppb, alternatively greater than about 20.0 ppb, alternatively greater than about 30.0 ppb, alternatively greater than about 0.1 parts per million ("ppm").

In addition to Kovat's and ODT properties mentioned above, other physical chemical properties of perfume raw materials that may render them useful as a FPC are molecular weight, vapor pressure, boiling point, flashpoint, heat of vaporization, viscosity, solubility parameters, and combinations of thereof.

Suitable FPCs may be highly volatile, low boiling, perfume ingredients. Exemplary FPC include iso-nonyl acetate, dihydro myrcenol (3-methylene-7-methyl octan-7-ol), linalool (3-hydroxy-3,7-dimethyl-1,6 octadiene), geraniol (3,7 dimethyl-2,6-octadien-1-ol), d-limonene (1-methyl-4-isopropenyl-1-cyclohexene, benzyl acetate, isopropyl myristate, and combinations thereof. Table 1 lists the approximate reported values for exemplary properties of certain FPCs. FIG. 1 shows the evaporation profile of certain FPCs in relation to commonly used VOCs in air freshening compositions.

TABLE 1

| FPC | Boiling Point (°C.) | MW | Clog P @ 25° C. | Flash point (°C.) | Vapor pressure | KI | ODT |
|---|---|---|---|---|---|---|---|
| Iso-Nonyl Acetate (CAS 58430-94-7) | 224.72 | 186.3 | 4.28 | 79.4 | 0.11 | 1178 | 12 ppb |
| Dihydro Myrcenol (CAS18479-58-8) | 197.66 | 156.3 | 3.03 | 76.1 | 0.1 | 1071 | 32 ppb |

TABLE 1-continued

| FPC | Boiling Point (° C.) | MW | Clog P @ 25° C. | Flash point (° C.) | Vapor pressure | KI | ODT |
|---|---|---|---|---|---|---|---|
| Linalool (CAS 78-70-6) | 205.1 | 154.3 | 2.549 | 78.9 | 0.05 | 1107 | 22 ppb |
| Benzyl Acetate (CAS 140-11-4) | 213.9 | 150.18 | 1.70 | 95.0 | 0.15 | 1164 | 29 ppb |

The total amount of FPCs in a perfume mixture may be greater than about 40%, alternatively greater than about 50%, alternatively greater than about 60%, alternatively greater than about 70%, alternatively greater than about 75%, alternatively greater than about 80%, alternatively from about 40% to about 100%, alternatively from about 45% to about 100%, alternatively from about 50% to about 100%, alternatively from about 60% to about 100%, alternatively from about 70% to about 100%, alternatively from about 75% to about 100%, alternatively from about 80% to about 100%, alternatively from about 85% to about 100%, alternatively from about 90% to about 100%, alternatively about 100%, by weight of the perfume mixture. In some embodiments, the perfume mixture may consist entirely of FPCs (i.e. 100 wt. %). In other embodiments, the composition may consist entirely of FPCs.

The FPC mixture may comprise iso-nonyl acetate, dihydromyrcenol, linalool, and benzyl acetate. In one embodiment, iso-nonyl acetate, dihydromyrcenol, linalool, and benzyl acetate may, individually, be present in an amount of about 25%, by weight of the perfume mixture, alternatively in a ratio of 1:1:1:1. In other embodiments, iso-nonyl acetate, dihydromyrcenol, linalool, and benzyl acetate may be present in the ranges shown in Table 2.

TABLE 2

| Perfume Raw Material | KI Value | Low wt. % | High wt. % |
|---|---|---|---|
| Benzyl Acetate | 1164 | 5 | 50 |
| Iso Nonyl Acetate | 1178 | 5 | 35 |
| Dihydro Myrcenol | 1071 | 5 | 45 |
| Linalool | 1107 | 15 | 45 |

FPC Mixtures 1 and 2 in Table 3 are provided for purposes of illustrating, non-limiting, exemplary FPC mixtures which may be used in a non-energized, wick-based air freshener.

TABLE 3

| Perfume Raw Material | KI Value | FPC Mixture 1 wt. % | FPC Mixture 2 wt. % |
|---|---|---|---|
| Benzyl Acetate | 1164 | 5 | 10 |
| Iso Nonyl Acetate | 1178 | 5 | 35 |
| Dihydro Myrcenol | 1071 | 45 | 20 |
| Linalool | 1107 | 45 | 35 |

Non-Functional Perfume Component

The composition of the present invention may include a non-functional perfume component or components. A non-functional perfume component is a perfume raw material that is utilized solely for its fragrance, scent, or hedonic benefits. Non-functional perfume components do not satisfy the properties of an FPC. Suitable non-functional perfume components are disclosed in U.S. Pat. Nos. 5,663,134; 5,670,475; 5,783,544; 5,939,060; and 6,146,621.

Use of FPCs at the levels recited herein may help modulate the evaporation profile of an entire perfume composition to provide perfume character consistency over the intended usage period in various systems. The use of FPCs does not interfere with the perfume characteristics of the non-functional perfume components that are included for their fragrance or hedonic benefits.

Active Agents

Active agents provide cleaning, surface care protection, fabric conditioning or softening, fabric refreshing, de-wrinkling, air freshening, air deodorizing, malodor removal, skin moisturizing, body deodorizing, or like benefits. An active agent does not include water or deionized water.

In an air freshening or fabric refreshing composition, the active agents may deliver a genuine malodor removal benefit. A genuine malodor removal benefit is defined as both a sensory and analytically measurable (such as by GC) malodor reduction. Thus, if the air freshening composition delivers a genuine malodor removal benefit, the air freshening composition will not function merely by using perfume to cover up or mask odors. If the air freshening product is provided with a malodor counteractant, the air freshening product may utilize one or more of several types of odor control mechanisms. One suitable malodor controlling agent is cyclodextrin, which is disclosed in U.S. Pat. Nos. 5,534,165; 5,668,097; 5,714,317; and 6,682,694.

Active agents might also include surfactants, emulsifiers, solubilizers, polymers, malodor counteractants such as cyclodextrin, hydrogen peroxide, buffers, zinc ions, etc. For example, suitable fabric conditioning/softening agents are disclosed in U.S. Pat. No. 5,139,687.

Product Forms

The composition of the present invention may be used with any apparatus known in the art to deliver fragrance to the atmosphere. Non limiting examples of such delivery apparatuses include air diffusers, whether energized or non-energized, with and without evaporative substrates (e.g. breathable membranes or wicks); coupled and decoupled piezoelectric systems; gel matrixes, etc. Suitable apparatuses include liquid electric systems disclosed in U.S. Pat. No. 7,223,361 and energized, piezo-electric systems in US 2009/0289127A1.

The composition may also be used with a passive air diffuser that includes a breathable membrane for diffusing the FPC mixture. A breathable membrane is a vapor permeable membrane that prevents free flow of liquid out of the membrane, thus addressing leakage problems. Suitable membranes include UHMWPE-type membrane optionally filled with silica as described in U.S. Pat. No. 7,498,369. Such UHMWPE membranes include Daramic™ V5, available from Daramic, Solupor®, available from DSM (Netherlands), and Teslin™ SP1100HD, available from PPG Industries, and combinations thereof. Other suitable breathable membranes include any permeable polymeric, thermoplastic, or thermoset material, including acetal, acrylic, cellulosic, fluoroplastic, polyamide, polyester, polyvinyl, polyolefin, styrenic, etc, alone, co-extruded, woven or non-woven, mixed or in combination with elastomers, rubber, solids, silicas, or combinations thereof. Also suitable are Hytrel™ available from Dupont or Lotryl™ available from Arkema.

The composition of the present invention may also be formulated for use in personal care products such as skin moisturizers, body deodorants, facial and body cleansers, baby wipes; surface care compositions such as hard surface cleaners, wood polishes, and automobile cleaners; fabric care compositions such as cleaners, softeners, de-wrinklers, and refreshers; and air freshening compositions including aerosols and sprays.

EXAMPLE

Weight loss profiles of FPC Mixtures 1 and 2 in Table 3, a FPC Control Mixture, and DPM are evaluated. Four glass bottles, each being identical to one another in material and configuration, are separately filled, using a pipette, with 5.5 mL of FPC Mixture 1 (shown in Table 3), FPC Mixture 2 (shown in Table 3), FPC Control Mixture (shown in Table 4) and DPM. A plug and wick assembly, Porex ZSF-7575, are attached to each bottle. The bottles are placed on a shelf in a bathroom lab with volume of 10 m$^3$ with 2 air changes per hour, controlled to 21+/−2 degrees Celsius. An initial weight is recorded and then subsequent weights are recorded after 4, 7, 12, and 15 days have elapsed. Weights are taken on a calibrated, leveled Ohaus Analytical Plus™ AP120 laboratory balance. Weight loss is calculated as follows:
where
$t_i$ and $t_j$=points in time;
$t_j-t_i$=the time interval between $t_i$ and $t_j$;
$E_{ij}$=Evaporation rate between time $t_i$ and $t_j$;
$W_i$=Weight in mg at time i;
$W_j$=Weight in mg at time j;

TABLE 4

| Perfume Raw Material | KI Value | FPC Control Mixture wt. % |
|---|---|---|
| Benzyl Acetate | 1164 | 7 |
| Iso Nonyl Acetate | 1178 | 24.5 |
| Dihydro Myrcenol | 1071 | 14 |
| Linalool | 1107 | 24.5 |
| d-Limonene | 1031 | 30 |

TABLE 5

| | Days Elapsed | Weight Loss Rate, mg/h | Cumulative Weight Lost, mg |
|---|---|---|---|
| DPM | 0 | 0.0 | 0 |
| | 4 | 2.3 | 209 |
| | 7 | 4.1 | 497 |
| | 12 | 2.9 | 824 |
| | 15 | 3.8 | 1090 |
| FPC Mixture 1 | 0 | 0.0 | 0 |
| | 4 | 2.9 | 268 |
| | 7 | 3.2 | 506 |
| | 12 | 2.5 | 798 |
| | 15 | 2.9 | 1000 |
| FPC Mixture 2 | 0 | 0.0 | 0 |
| | 4 | 4.6 | 423 |
| | 7 | 4.8 | 797 |
| | 12 | 3.9 | 1242 |
| | 15 | 4.0 | 1522 |
| FPC Control Mixture | 0 | 0.0 | 0 |
| | 4 | 7.5 | 676 |
| | 7 | 6.6 | 1172 |
| | 12 | 6.1 | 1878 |
| | 15 | 6.5 | 2343 |

The weight loss of DPM, FPC Mixture 1, FPC Mixture 2, and FPC Control Mixture are shown in FIG. 1. The weight loss curve for these mixtures demonstrate that the FPC Mixtures 1 and 2 are comparable to DPM and more consistent over time than FPC Control Mixture for fragrancing the atmosphere.

The composition of the present invention can comprise, consist of, or consist essentially of the elements and limitations of the invention described herein, as well any of the additional or optional ingredients, components, or limitations described herein.

Every numerical range given throughout this specification will include every narrower numerical range that falls within such broader numerical range, as if such narrower numerical range were all expressly written herein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 6.1, 3.5 to 7.8, 5.5 to 10, etc.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An article of manufacture for air freshening comprising:
an evaporative substrate selected from the group consisting of wicks, breathable membranes, and combinations thereof; and
a reservoir;
a composition contained in said reservoir, wherein said composition comprises a perfume mixture, said perfume mixture comprises a FPC mixture, said FPC mixture comprises about 75% to about 100%, by weight of said perfume mixture, of iso-nonyl acetate, dihydro myrcenol, linalool, and benzyl acetate, wherein said iso-nonyl acetate is present in an amount of about 5% to about 35%, by weight of said FPC mixture, wherein said dihydro myrcenol is present in an amount of about 5% to about 45%, by weight of said FPC mixture, wherein said linalool is present in an amount of about 15% to about 45%, by weight of said FPC mixture, and wherein said benzyl acetate is present in an amount of about 5% to about 50%, by weight of said FPC mixture, and wherein said composition is substantially free of a VOC.

2. The article of manufacture of claim 1 wherein said composition consists of iso-nonyl acetate, dihydro myrcenol, linalool, and benzyl acetate.

3. The article of manufacture of claim 1 wherein said composition further comprises an active agent.

\* \* \* \* \*